United States Patent [19]

Pflaum et al.

[11] Patent Number: 5,853,720
[45] Date of Patent: Dec. 29, 1998

[54] COMBINED PROCESS FOR THE PURIFICATION OF VANCOMYCIN HYDROCHLORIDE

[75] Inventors: Zlatko Pflaum, Kranj; Robert Turkalj, Kamnik, both of Slovenia

[73] Assignee: LEK, tovarna farmacevtskih in kemicnih izdelkov, d.d., Ljubljana, Slovenia

[21] Appl. No.: 875,443

[22] PCT Filed: Feb. 6, 1996

[86] PCT No.: PCT/SI96/00003

§ 371 Date: Jul. 28, 1997

§ 102(e) Date: Jul. 28, 1997

[87] PCT Pub. No.: WO96/24615

PCT Pub. Date: Aug. 15, 1996

[30] Foreign Application Priority Data

Feb. 7, 1995 [SI] Slovenia .............. P-9500039

[51] Int. Cl.⁶ .............. A61K 38/12; C07K 5/12
[52] U.S. Cl. .............. 424/124; 530/344
[58] Field of Search .............. 530/344; 424/124

[56] References Cited

U.S. PATENT DOCUMENTS 5,235,037  8/1993  Krishnan .............. 530/322

OTHER PUBLICATIONS

Subramanian, G. et al.: Displacement Chromatography of biomolecules. J. of Chromatography, vol. 439, pp. 341–351, 1988.

*Primary Examiner*—Alan L. Rotman
*Assistant Examiner*—Charanjit S. Aulakm
*Attorney, Agent, or Firm*—Pollock, Vande Sande & Amernick

[57] ABSTRACT

The present invention discloses a new process for the purification of vancomycin hydrochloride by combining preparative chromatography on a silica gel column and the precipitation with ethanol from a salt-water-ethanolic solution without intermediary filtering, whereby the chromatographic purity of the product is improved.

The chromatography is carried out on a column containing a silica gel stationary phase and an alkaline water-methanolic mobile phase at defined pH, mobile phase flow and temperature as well as the amount and concentration of vancomycin hydrochloride. The process is distinguished by the yield and chromatographic purity of the obtained product of about 93% area.

Vancomycin hydrochloride purified according to the present invention is useful for peroral as well as parenteral administration since the portion of impurities it contains is for one third smaller than in hitherto available product.

17 Claims, No Drawings ing fermentation, isolation and purification, sometimes a product with a more distinctive colour and with an unpleasant odour is obtained and also the yield and purity are reduced, which cannot be improved even if the process is repeated several times.
COMBINED PROCESS FOR THE PURIFICATION OF VANCOMYCIN HYDROCHLORIDE

TECHNICAL FIELD

International Patent Classification:

C 07 K 9/10; C 07 K 3/20; C 07 K 3/24; C 07 K 3/28

This application is a 371 of PCT1SI 96/00003, which is now published as WO96/24615 on Aug. 15, 1996.

The present invention relates to a new process for the purification of vancomycin hydrochloride, which combines the preparative chromatography on a silica gel column containing an alkaline water-methanol mobile phase and the precipitation with ethanol from a salt-water-ethanolic solution, whereby improved chromatographic purity of the product is achieved, making it available both for peroral and parenteral administration.

Vancomycin is a tricyclic amphoteric glycopepitide antibiotic in a salt (hydrochloride) form having the empirical formula $C_{66}H_{75}Cl_2N_9O_{24}\cdot HCl$ and the molecular weight of 1.486. The preparation of vancomycin by fermentation of the microorganisms *Amycolatopis orientalis* (previously *Nocardia orientalis*) is described in more detail in U.S. Pat. No. 3,067,099 (filed in 1955) and in WO 91/08,300 (filed in 1990). Lyophilized vancomycin hydrochloride has an off-white colour and with water it forms a clear solution having a pH between 2.5 and 4.5.

Vancomycin hydrochloride is particularly used for the initial treatment of serious or severe infections caused by staphylococci resistant against β-lactam antibiotics as well as in patients who are penicillin-sensitive or do not respond to penicillins and cephalosporines.

Vancomycin hydrochloride is commercially available in oral (solution and capsules/pulvules) and parenteral (sterile intravenous solution in vials) forms.

Oral use of vancomycin hydrochloride is only allowed in treating staphylococcal enterocolitis where the parenteral form is not effective. For all other types of indications only parenteral use is relevant.

Vancomycin hydrochloride alone or in combination with other aminoglycosides is also useful in treating staphylococcal, streptococcal, enterococcal or diphtherial endocarditis.

To reduce the possibility of side effects a high chromatographic purity of antibiotics is very important in some kinds of their usage, which cannot be achieved by hitherto existing purification processes. By the process according to the present invention the impurity portion in the sample has been reduced for one third.

TECHNICAL PROBLEM

In the preparation of vancomycin consisting of a multistage process involving fermentation, isolation and various means of purification, sometimes a product with a more distinctive colour and with an unpleasant odour is obtained and also the yield and purity are reduced, which cannot be improved even if the process is repeated several times.

Since vancomycin represents a very interesting and valuable product, a constant need for new processes for effective isolation and purification thereof exists. By the use of the most hitherto known processes and also by a multiple repetition of the processes, the portion of several kinds of impurities cannot be reduced so as to obtain vancomycin with an improved purity grade.

Therefore it is the aim of present invention to prepare vancomycin hydrochloride useful both for peroral and parenteral administration of at least an equal or better quality as found in other commercially available products.

PRIOR ART

From patent and other literature a number of methods for the preparation of glycopeptide antibiotics from the fermentation medium as well as for the purification of fermentation products are known, which include precipitation processes using NaOH (EP 323,150, U.S. Pat. No. 5,037,652, JP 5,244,964), formation of phosphates (EP 145,484) or complexes with peptides (U.S. Pat. No. 4,667,024) or imidazole (U.S. Pat. No. 4,868,285) as well as processes for adsorption onto different polymer resins (U.S. Pat. No. 4,440,753, U.S. Pat. No. 4,845,194, U.S. Pat. No. 4,874,843, U.S. Pat. No. 5,149,784, WO 91/08,300, U.S. Pat. No. 5,258,495 or WO 93/21,207).

U.S. Pat. No. 4,868,285 cites the precipitation of vancomycin hydrochloride with ethanol following the dissolution of the complex with imidazole.

WO 91/08,300 discloses a process for microbiological preparation of vancomycin antibiotic via aerobic fermentation by the use of several cultivation strains and cultures. The isolation of vancomycin may be performed to the manner known "per se" or by a process comprising ion exchange chromatography for the separation of the vancomycin antibiotic, concentration by the use of reverse osmosis and ultrafiltration.

U.S. Pat. No. 5,235,037 discloses a process particularly suitable for vancomycin, which is based on the isolation of vancomycin via precipitation from a water solution having a pH 5–9 by adding different anorganic salts such as NaCl (5–10%), at a temperature of 20°–25° C., the precipitation taking place in a period of 16–24 hours at a concentration of vancomycin of 5–200 g/l. Subsequently, the product is filtered. This process is useful in any stage of the preparation of vancomycin either for the complete fermentation broth or for additional purifying of partly purified (by filtration and adsorption chromatography) vancomycin after elution with a cation exchange polymer resin consisting of styrene and divinylbenzene. A maximum yield is obtained already at diluted water solutions (5–6 g/l), however, at concentrations of 100–500 g/l a better filtration is achieved. This patent also states the removal of vancomycin from the obtained precipitate by a repeated dissolution of the precipitate in a water HCl solution (i.e. at pH=2) and precipitation by the addition of suitable "non-solvent" for vancomycin such as ethanol or isopropanol. The product is a highly pure vancomycin in the form of a hydrochloride salt (the purity grade significantly depends upon the purity of the starting solution). The filtration runs readily and the obtained addition salt is useful for parenteral formulations.

TECHNICAL SOLUTION

The manufacturers of the antibiotics are constantly faced with the need to ensure a high yield of a product having high chromatographic purity. Therefore the improvement of the purification process for vancomycin hydrochloride by a combination of preparative chromatography on a silica gel column and of the precipitation with ethanol from a salt-water-solution according to the present invention represents an essential improvement of the prior art methods, since the impurity portion in the resulting substance is lower than or, at the most, equal to one of the purest commercially available sample known hitherto.

The aim of the present invention is to improve the purification process for vancomycin hydrochloride from the stage of the partly purified concentrate on by combining preparative chromatography on a silica gel column and the precipitation with ethanol from a salt-water-ethanolic solution. The whole process is carried out as follows:

The fermentation broth with the flow rate 0.5–1 m³/h is continuously pumped from the fermenter to the microfiltration device, wherein the solid portion of the broth is concentrated and washed with demineralized water flowing with the rate of 0.8–1.8 m³/h, whereby the solid protion is separated from the permeate solution containing the majority of vancomycin. A constant value of pH=7 of the permeate solution is maintained by a continuous addition of HCl. The yield of microfiltration is 90–95%.

Then the adsorption of vancomycin at pH=7 from the permeate solution after microfiltration onto 2.5 m³ of Amberlite XAD 16 resin (20 g of vancomycin can be bound to a 1 l of the resin) at a flow rate of 0.1–2.5 m³/h is performed. Subsequently the coloured impurities and anorganic salts are washed out with demineralized water under the addition of 50% NaOH in an amount adequate to adjust the pH to 10 at a flow rate of 5–10 m³/h, followed by washing with 20% alkaline methanol (50% NaOH is added to adjust the pH to 10) at a flow rate of 2.5 m³/h. Then the elution of vancomycin from the resin is started by using 20% acidic methanol (acetic acid is added) at a flow rate of 1 m³/h and at a pH of 2.7–2.8.

By reverse osmosis the removal of 20% acidic methanol from the combined eluates is performed in order to reduce their volume from 8–15 m³ to 0.8 m³.

HCl is added to the concentrate under washing with 15 m³ of demineralized water during the reverse osmosis (to maintain the pH at 2.7–3.0) and then it is concentrated to 450 l. In this process the displacement of acetate aniones by chloride aniones occurs, resulting in the conversion of vancomycin into vancomycin hydrochloride. Acetic acid used in the elution is washed out over a membrane. The concentrate obtained from reverse osmosis is cooled and active carbon (300 g per 1 kg of vancomycin) is added thereto. After stirring for 8–12 hours the obtained suspension is filtered on a filter press and washed with demineralized water. A discoloured product with a concentration of 6–12% is obtained.

Vancomycin hydrochloride dissolved in water is applied onto a preparative column containing a silica gel stationary phase and an alkaline water/methanolic mobile phase.

However, to achieve a sucessful purification it is very important to select an aproppriate flow rate of the mobile phase through the column and its pH value as well as the temperature in every stage of the purification on the column. Namely, at a low flow rate, the presence of vancomycin hydrochloride in the alkaline mobile phase is longer, which results in a greater possibility for its decomposition, whereas at a high flow rate the kinetics of purification is not appropriate. The elution of vancomycin at a too low pH value occurs slower, whilst at a too high pH value rapid elution of vancomycin along with other newly formed impurities occurs.

The product obtained from the column is separated into two fractions by the use of a UV detector:

| Fraction | Conc. of vancomycin.HCl | Chromatographic purity (area) |
|---|---|---|
| main | above ≈ 1.5 g/l | mean 93% |
| side | up to ≈ 1.5 g/l | up to 90% |

The greatest stability of vancomycin hydrochloride exists at a pH value between 2.5 and 5.5, but not in an alkaline medium, therefore it is necessary to acidify the main fraction to pH=3–5 with diluted (5%) HCl (neutralization of ammonium hydrogen carbonate). The other possibility is a substitution of ammonium cations with hydrogen cations by ion exchange.

Thereafter the following stages are performed:
an increase of vancomycin hydrochloride concentration to about 50 g/l by reverse osmosis;
depyrogenation of the concentrate by ultrafiltration;
diafiltration (removal of formed $NH_4Cl$) by reverse osmosis simultaneously with concentrating to a final concentration of about 100 g/l at a pH of about 3;
discoloration with active carbon (10–15% with regard to vancomycin hydrochloride) under cool conditions;
preparation of a solid product by lyophilization in a spray dryer or by precipitation.

By purification on a silica gel column a chromatographic purity of vancomycin hydrochloride in main fraction of about 93% area is achieved, the other coloured impurities are removed e.g. by the use of active carbon. By this process the portion of the majority of impurities is reduced for more than 40%.

Since in side fractions (content of vancomycin hydrochloride up to about 1.5 g/l and chromatographic purity up to 90% area), owing to their great portion of impurities, it is not possible to continue the purification by chromatography, additionally, the precipitation with ethanol from a salt-water-ethanolic solution is introduced and subsequently the product is repeatedly purified by preparative chromatography on a silica gel column.

Side fractions obtained by purification of vancomycin hydrochloride on silica gel column are acidified to pH≈3, then desalted in the reverse osmosis and concentrated to a concentration of 8% with regard to vancomycin hydrochloride. To this solution an equal amount by volume of ethanol and of 10–20% NaCl with regard to the amount of 8% vancomycin solution is added. From the newly obtained solution vancomycin hydrochloride is precipitated with a threefold amount of ethanol with regard to the used amount. The obtained suspension is cooled and filtered. The product filters well.

The discoloured concentrated solution of vancomycin hydrochloride is dried in a spray dryer at a temperature of the inlet air of 115°–130° C. and the temperature of the outlet air of 85°±5° C.. Usually, the content of water in vancomycin hydrochloride is about 4%, therefore it is additionally dried in a rotation vacuum dryer at a temperature of 45°–50° C. to obtain a dry solid product.

At the precipitation with ethanol from the salt-water-ethanolic solution, the filtration of the precipitate occurs easier and more rapidly under an increased (improved) chromatographic purity, whose percentage of increase depends upon the starting chromatographic purity (inverse proportionality) and the type of impurities. Chromatographic purity of the product after column chromatography is increased to about 93%. The portion of the majority of impurities is decreased for more than 40%.

The filtered precipitate can be:
a) desalted in reverse osmosis or by ion exchanger and repeatedly applied on a silica gel column or b) desalted and lyophilized for bulk by the addition of 12% of ethanol to the most in order to obtain the final product.

The total yield of the purification of the main and side fractions applied to the column is up to 80%.

By the process of the present invention there is obtained vancomycin hydrochloride having such a chromatographic purity that it can be used for peroral and parenteral administration.

The present invention is illustrated but in no way limited by the following two examples.

EXAMPLE 1

Chromatographic purification of vancomycin hydrochloride on silica gel column

The main fraction of vancomycin hydrochloride is purified by preparative chromatography under the following parameters:

vancomycin hydrochloride: concentration 77 g/l; pH=2.85; permeability of 5% solution $T_{405}$=57.3%;
column size: 30×80 cm;
stationary phase: silica gel, particle size 100–200 μm having 6 nm pores;
ratio of vancomycin to silica gel by weight: 1:100;
mobile phase: aqueous (0.35% $NH_4HCO_3$ in 7% methanol);
flow rate: 30 l/h;
temperature: 15° C.

The deposit was dissolved in 3.5 l of demineralized water, then applied onto the column and subjected to chromatography.

The main fraction was selected by the use of UV detector 120 l with the content of 1.82 g/l and chromatographic purity 93.3% area. The yield was 80%.

EXAMPLE 2

Purification of vancomycin hydrochloride by the precipitation method from salt-water-ethanolic solution The side fractions of vancomycin hydrochloride were also purified by precipitation with ethanol from salt-water-ethanolic solution.

10 g of vancomycin hydrochloride having a 80% content and chromatographic purity 83.6% area was dissolved in water, thereto water q.s. ad volumen 100 m was added. For the purpose of salting out, 10 g of NaCl and 150 ml of absolute ethanol were added and it was stirred until the solution was clarified. Another 250 ml of absolute ethanol were added thereto and the obtained precipitate was left to stand overnight at +4° C. and then filtered. Vancomycin hydrochloride was desalted in reverse osmosis (45×75 cm) and an amount of 6 l was applied twice.

8.7 g of a product with a content of 65.7% and a chromatographic purity of 90.3% area were obtained.

Yield: 71.4%.

We claim:

1. A new process for the purification of vancomycin antibiotics, characterized in that it combined preparative chromatography on a silica gel column containing an alkaline water-methanolic mobile phase and precipitation with ethanol from a salt-water-ethanolic solution for side fractions, which comprises the following stages:

a) concentrating the acidified combined side fractions of the antibiotic having concentrations up to about 1.5 g/l by reverse osmosis;

b) addition of NaCl and stirring to achieve the dissolution of the salt and the crystallization of the antibiotic;

c) addition of ethanol to the resulting suspension at room temperature to cause first the dissolution of the crystallized antibiotic and a further addition of ethanol (totally four times more ethanol than water) to initiate the precipitation of the antibiotic;

d) the cooling of the obtained suspension to about 5° C. and centrifugation;

e) desalting of the antibiotic in reverse osmosis and continuing the process as used for the main fraction.

2. A process according to claim 1, characterized in that the final product is prepared by the precipitation from a salt-water-ethanolic solution.

3. A process according to claim 2, characterized in that the final product is dried in a spray dryer.

4. A process according to claim 2, characterized in that the final product is prepared by lyophilization from the ethanolic solution of the antibiotic.

5. A process according to claim 4, characterized in that the lyophilization is carried out by the addition of 12% of ethanol at the most.

6. A process according to claim 1, characterized in that it is used for the purification of vancomycin and vancomycin hydrochloride.

7. A process according to claim 1, characterized in that the concentration of the antibiotic applied to the column and prior to the beginning of crystallization is from about 50 to about 120 g/l.

8. A process according to claim 7, characterized in that the concentration of the antibiotic applied to the column and prior to the beginning of crystallization is about 80 g/l.

9. A process according to claim 1, characterized in that the ratio by weight of the antibiotic to silica gel on the column is about 1:100.

10. A process according to claim 1, characterized in that the mobile phase is 0.35% of $NH_4HCO_3$ in 7% methanol.

11. A process according to claim 1, characterized in that the mobile phase flow is between about 20 l/min and about 100 l/min.

12. A process according to claim 1, characterized in that the pH of the mobile phase is between about 7.9 and about 8.5.

13. A process according to claim 1, characterized in that the temperature in the column is about 15° C.

14. A process according to claim 1, characterized in that the crystallization is performed by the use of about 10 to about 20% of NaCl with regard to water.

15. A process according to claim 1, characterized in that the crystallization is performed by the use of about 15% of NaCl with regard to water.

16. A process according to claim 1, characterized in that an antibiotic of such a purity is obtained that it can be used for peroral or parenteral administration.

17. The process according to claim 1 wherein the pH of said acidified combined side fractions is 2.7–3.0 during said reverse osmosis.

* * * * *